United States Patent [19]

Inoue et al.

[11] 4,195,177
[45] Mar. 25, 1980

[54] HYDROXYALKYL-ETHERIFIED GLYCOLIPID ESTER

[75] Inventors: Shigeo Inoue, Saitama; Yoshiharu Kimura, Ichikawa; Manzo Kinta, Funabashi, all of Japan

[73] Assignee: Kao Soap Co., Ltd., Tokyo, Japan

[21] Appl. No.: 962,664

[22] Filed: Nov. 21, 1978

[30] Foreign Application Priority Data

Mar. 3, 1978 [JP] Japan .................. 53/24306

[51] Int. Cl.² .............. C07H 15/08; C07H 13/04
[52] U.S. Cl. ......................... 536/116; 536/4; 536/115; 536/119; 536/120; 424/361
[58] Field of Search .............. 536/4, 115, 116, 119, 536/120

[56] References Cited

U.S. PATENT DOCUMENTS

| | | | |
|---|---|---|---|
| 2,652,394 | 9/1953 | DeGroote | 536/120 |
| 2,927,919 | 3/1960 | Anderson | 536/120 |
| 3,022,335 | 2/1962 | Lundsted | 536/120 |
| 3,305,542 | 2/1967 | Carlberg et al. | 536/120 |
| 3,442,888 | 5/1969 | Degginger et al. | 536/120 |
| 3,459,733 | 8/1969 | Byrd, Jr. et al. | 536/119 |
| 3,535,307 | 10/1970 | Moss et al. | 536/120 |

*Primary Examiner*—Johnnie R. Brown
*Attorney, Agent, or Firm*—Oblon, Fisher, Spivak, McClelland & Maier

[57] ABSTRACT

A hydroxyalkyl-etherified glycolipid ester represented by the formula (I),

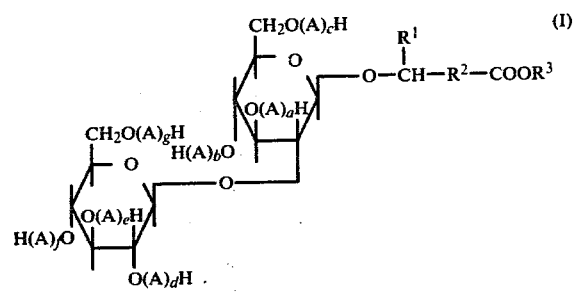

wherein $R^1$ represents a methyl group or a hydrogen atom, $R^2$ represents a saturated or unsaturated hydrocarbon group having 11 to 15 carbon atoms when $R^1$ is a methyl group, $R^2$ represents a saturated or unsaturated hydrocarbon group having 12 to 16 carbon atoms when $R^1$ is a hydrogen atom, $R^3$ represents a saturated or unsaturated hydrocarbon group having 1 to 20 carbon atoms, A represents $-CH_2-CH_2-O-$ or

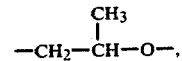

and a,b,c,d,e,f and g represent integers from 1 to 60 in the sum total.

4 Claims, No Drawings

HYDROXYALKYL-ETHERIFIED GLYCOLIPID ESTER

BACKGROUND OF THE INVENTION

1. Field of the Invention

This invention relates to a novel wax-like substance possessing surface activity characteristics, and to a process for producing the same. More particularly, the invention relates to hydroxyalkyl-etherified glycolipid esters represented by formula (I),

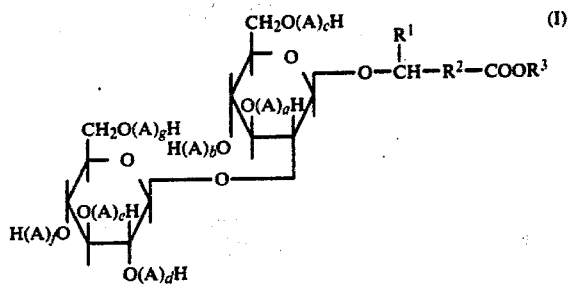

wherein $R^1$ represents a methyl group or a hydrogen atom, $R^2$ represents a saturated or unsaturated hydrocarbon group having 11 to 15 carbon atoms when $R^1$ is a methyl group and $R^2$ represents a saturated of unsaturated hydrocarbon group having 12 to 16 carbon atoms when $R^1$ is a hydrogen atom, $R^3$ represents a saturated or unsaturated hydrocarbon group having 1 to 20 carbon atoms, A represents $-CH_2-CH_2-O-$ or

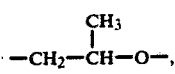

and a,b,c,d,e,f and g represent integers whose sum ranges from 1 to 60, and represented by formula (II),

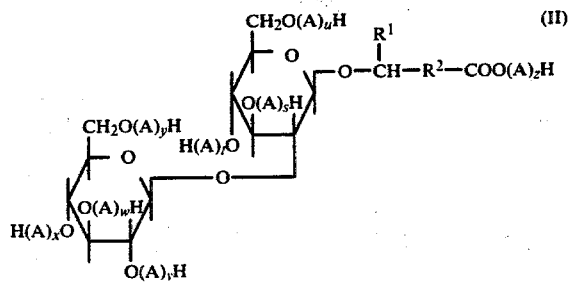

wherein $R^1$, $R^2$ and A are the same as defined above, and s,t,u, v,w,x,y, and z represent integers whose sum ranges from 1 to 60.

2. Description of the Prior Art

Esters of a long-chain fatty acid and a long-chain alphatic alcohol, long-chain hydrocarbons, glycerides, lanolin and the like, all known materials, are wax or grease-like materials. The esters have been widely used as glazing materials and oily substances for leather, cosmetics and ointments, lubricants for fibers, machinery, stationery, printing, rust inhibition and insulation and have been used in metal processing. In recent years, was has often been used in emulsified form with a surface active agent in view of its safety and easy handling. However, formulation technique of a high degree is required for emulsification of wax because the wax characteristics depend directly upon such formulation technique.

Extremely high formulation techniques only permit wax to exhibit all of its inherent characteristics, but this involves such difficulty. Hence, there has been a strong desire for the development of a wax possessing surface activity.

Wool wax, which is known under the name of lanolin, includes in its structure a peculiar ester bond formed between the long-chain branched fatty acid and the long-chain branched aliphatic alcohol or steroid alcohol, it is a wax substance having both an excellent wax-like property and a proper emulsifying ability. However, wool wax is a mysterious naturally occurring compound and does not find wide applicability partly because its combination with other materials require highly advanced techniques and partly because the amounts used are limited because of its peculiar animal smell.

In view of that situation, the present inventors have conducted a wide variety of studies on the development of a compound possessing a surface activity and wax-like properties, and have found that a glycolipid ester represented by the formula (III) exhibits the desired activity and properties.

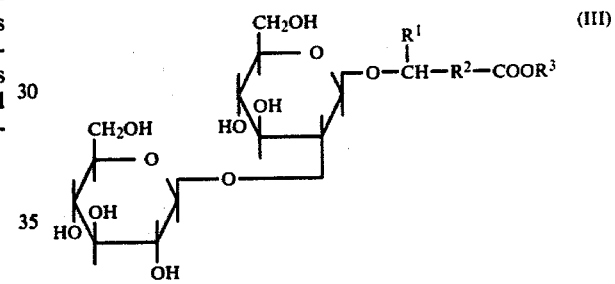

wherein $R^1$, $R^2$ and $R^3$ are the same as defined above.

However, the glycolipid ester of the formula (III) lacks heat stability at high temperatures and viscosity. The reason is that the hydroxy group of the sugar moiety of this compound exists in a free form, thereby resulting in reduced adhesiveness, lubricity, flexibility and plasticity.

A further study was made in order to improve the above-mentioned properties arising from the sugar structure and as a result various derivatives of the glycolipid ester of formula (III) have been synthesized by chemical modification of the hydroxy groups. After investigating the characteristics of these derivatives, it has been found that the compound of formula (I) obtained by modification of the hydroxy groups with hydroxyalkyl groups, and the compound of formula (II) produced by modification of the hydroxy groups and carboxyl group with hydroxyalkyl groups possess the above desired characteristics. A novel process for producing the same has also been discovered.

SUMMARY OF THE INVENTION

It is, therefore, one object of this invention to provide a hydroxyalkyl-etherified glycolipid ester possessing excellent surface activity.

It is another object of the invention to provide a process for producing the same.

The compounds of the formulae (I) and (II) are produced according to the present invention, as shown in the following reaction scheme, by reacting a glycolipid ester of the formula (III) or glycolipid of the formula (IV) with an alkylene oxide in the presence of an alkali catalyst.

(Reaction Equation I)

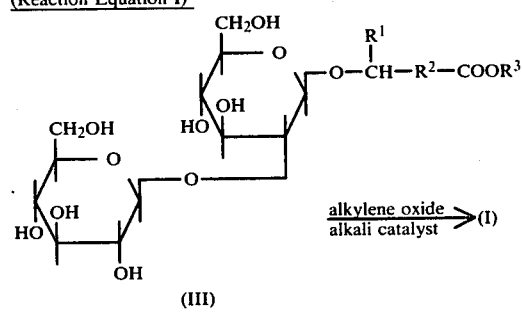

(III)

$R^1$, $R^2$ and $R^3$ are the same as defined above.

(Reaction Equation II)

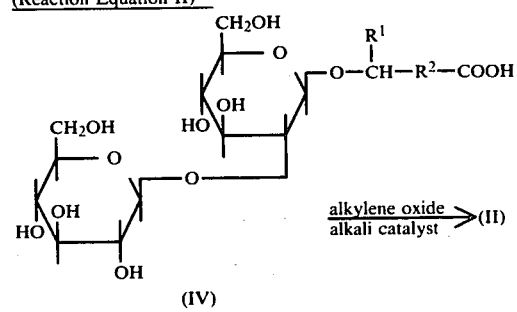

(IV)

$R^1$ and $R^2$ are the same as defined above.

DETAILED DESCRIPTION OF THE PREFERRED EMBODIMENTS

The starting material of formula (III) or a glycolipid ester can be produced by a method found by the present inventors. For example, Sophorolipid is subjected to methanolysis and methylation reactions by reaction with methanol in an acid to produce a glycolipid methyl ester which is further converted into the compound of formula (III) by reacting the glycolipid methyl ester with an alcohol of the formula, ROH, wherein R is a saturated or unsaturated hydrocarbon group having 2 to 20 carbon atoms, and by subject the resulting reaction mixture to an ester interchange reaction. The starting material of formula (IV) or glycolipid is produced by hydrolyzing the glycolipid methyl ester.

Suitable alkylene oxides which are useful in the invention include ethylene oxide and propylene oxide.

The compounds of formulas (III) and (IV) readily react with alkylene oxides under the conditions applicable to a normal addition reaction. However, an alkali catalyst is preferably used because glucoside bonds of the disaccharide may be cleaved by acid. Suitable alkali catalysts which are useful in the invention include sodium metal, potassium metal, sodium hydroxide, potassium hydroxide, sodium alcoholate, potassium alcoholate and the like. The alkali catalyst is used preferably in an amount of from 0.2 to 1.0 in terms of its weight percent to the glycolipid or glycolipid ester. The reaction is carried out preferably at a temperature ranging from 70° to 120° C., especially from 100° to 120° C.

The catalyst may be used singly or in combination.

The reaction progress can be observed by measuring the pressure in the reactor or by quantitatively analyzing the reaction products so that an adduct having any predetermined addition number can be produced.

The hydroxyalkyl-etherified glycolipid ester thus obtained according to the invention does not undergo any structural degeneration or deterioration in a preservation test at 250° C. for 48 hours because the hydroxy groups in the sugar structure are combined with the hydroxyalkyl groups through the stable ether bonds. Moreover, a variety of substances having both wax-like and hydrophilic properties and surface activities suitable for any desired purposes of application can be produced by varying the species of the glycolipid ester and addition mole number since any addition mole number of the alkylene oxide may be specified.

The characteristics of the typical compounds of the formulae (I) and (II) are shown in Table 1.

Table 1

| Ester Residue | Adduct | Characters |
|---|---|---|
| $CH_3$ | EO | Readily soluble in water. HLB value is on the order of 20. Greatly effective as a cleanser. 30 moles of adduct is fairly soluble in hydrocarbon solvents and mixes well with wax substance. Suitable as an auxiliary agent for lubrication and softening by wax |
| $C_{12}H_{25}$ | EO | Soluble in warmed water. Emulsified and dispersed at low temperature. Wax-like substance having 13 to 15 HLB values. Having a great mixing ability with wax substance. Useful as a softening lubricant for fiber or an emulsifying agent for an emulsified type of glazing material and a wax agent. Has an especially desirable effect when applied as a moisturizer for cosmetics. |
| $C_{18}H_{37}$ | EO | Viscous paste substance and having a property similar to lanolin. It is a fiber-like oil and has a good mixing ability with wax substance. Can be used as an emulsifying agent, a glazing material, leather oil, a softening lubricant for fiber, oil for cosmetics and ointments, especially when used as a moisturizer for ointments and cosmetics, it has a particularly desirable effect. |
| Oxy-ethylene | EO | Readily soluble in water. HLB value is more than 20. Effective as a cleanser. Exerts an enhancing effect on a lubricant and softening agent. Effective as a moisturizer for cosmetics. |
| $CH_3$ | PO | Only slightly soluble in water. Viscous paste. Emulsified and dispersed on a warm bath. Has a highly excellent mixing ability with higher fatty acids, higher alcohols and the like, and a good adhesiveness on the surface of solid. Can be used as a fat-addition and a softening lubricant for leather, skin and fiber. |
| $C_{12}H_{25}$ | PO | Only more slightly soluble in water. Wax-like paste having an extensibility and lubricating ability. Mixes well with hydrocarbon solvents and with various wax homogeneously. When used with wax, properties possessed by wax is enhanced because it lowers the viscosity of solid waxes and glycerides, and softens them. |
| $C_{18}H_{37}$ | PO | Insoluble in water. Elastic paste-like wax. Has an extremely excellent mixing ability with hydrocarbon solvent and wax. Has a wide application, a quality-improving ability for wax, fat-addition, softening lubricant, oil |

Table 1-continued

| Ester Residue | Adduct | Characters |
|---|---|---|
| | | for cosmetics, ointments, oil for metal-processing, machine oil, rust inhibitor, oil for stationary and oil for printing. |
| Oxy-propylene | PO | Only slightly soluble in water. Viscous paste. Emulsified and dispersed on a warm bath. Has an excellent mixing ability with higher fatty acids, higher alcohols and the like, and a good adhesiveness on the surface of a solid. Effective as a fat-addition and softening lubricant for leather, skin and fiber. |

EO denotes ethylene oxide, and PO denotes propylene oxide in Table 1.

It is apparent, from the above, that the present compound of formula (I) possesses an extremely excellent effect when applied as an oil for cosmetics and leather, and as a softening lubricant for fiber. Especially when used in an amount of from 2 to 10% by weight for cosmetics, the compound serves as an emulsifying agent, and it imparts elasticity and lubricity to the skin because of its affinity to the skin.

The present invention is illustrated below in further detail with reference to some Inventive Examples, but the invention is not limited to these Inventive Examples.

REFERENCE EXAMPLE 1

(i) To a mixture of 1500 g of glucose, 75 g of a yeast extract and 15 g of urea was added water to adjust the whole volume to 15 l, and the resulting mixture was sterilized and used as a fermentation liquid. To this liquid was inoculated *Torulopsis bombicola* which had been cultured on the same medium as above at 30° C. for 48 hours. The fermentation was started with stirring at a speed of 300 rpm and aerated at 0.33 VVM at 20° C. The culturation was conducted for 24 hours after inoculation of the microorganisms, and 150 g of a tallow oil was added at intervals of 24 hours. The added tallow oil amounted to 900 g. After the final addition, the culturation was continued for 24 hours. The culturation time amounted to 168 hours. A Sophorolipid layer which precipitated on the bottom of the fermentor was collected by decantation to give 1300 g of Sophorolipid in a paste form at room temperature which had a water content of about 50%.

(ii) The thus obtained 100 g of Sophorolipid and 2.5 g of polypropylene glycol having an average molecular weight 200 were placed in a 200 ml round bottom flask equipped with a stirrer and a Liebig condenser. The mixture was evaporated with stirring at 80° C. in an oil bath under a reduced pressure of 250 mmHg to eliminate water. After evaporation for about 2 hours, water was completely removed by distillation, and the water content was found to be less than 1%.

(iii) To the thus obtained Sophorolipid-polypropylene solution were added 150 g of methanol and then 2.5 g of sulfuric acid. The resulting mixture was reacted at 40° C. ±2° C. for 90 minutes. The reaction progress was observed by thin layer chromatography on silica gel [solvent: chloroform-methanol-acetic acid (75:20:5)], and the reaction was regarded as having reached completion when many spots shown by the starting material or Sophorolipid converged on the thin layer chromatography.

After the completion of the reaction, the reaction solution was neutralized with potassium hydroxide and filtered with filter paper. The filtrate was placed in a round bottom flask equipped with a Liebig condenser, and methanol and methyl acetate were distilled off to give 48 g of a brown paste mixture which contained 94% of [(2′-O-β-D-glucopyranosyl-β-D-glucopyranosyl)oxy]-alkane acid and -alkene acid methyl ester, and polypropyleneglycol. This mixture was purified by column chromatography on silica gel, and there were obtained pure [(2′-O-β-D-glucopyranosyl-β-D-glucopyranosyl)oxy]-alkane acid and -alkene acid methyl esters.

IR (cm$^{-1}$): 1740 (>C=O ester); 1380~3200 (—OH sugar); 900~750 (glucopyranose ring).

NMR [δ(pyridine)]: 1.1~1.6 (—CH$_2$—CH$_2$—); 3.6 (—O—CH$_3$); 3.5~5.0 (sugar); 5.5 (—CH=CH—unsaturated fatty acid).

Oil Characterization Analysis:
Acid value: 0
Hydroxy value: 615
Saponification value: 88
Ester value: 87 This product was degraded in a 5 N hydrochloric acid-methanol solution to give 2 moles of a methyl glycoside and 1 mole of a hydroxyfatty acid methyl ester, which was quantitatively analyzed by gas chromatography.

INVENTIVE EXAMPLE 1

A 100 g amount of the mixture of [(2′-O-β-D-glucopyranosyl-β-D-glucopyranosyl)oxy]-alkane acid and -alkene acid methyl esters, and polypropyleneglycol obtained in Reference Example 1 was placed in an autoclave together with 0.25 g of potassium hydroxide, and the mixture was reacted at 100°–120° C. for 6 hours with an amount of ethylene oxide gas corresponding to the addition mole number shown in Table 2 being passed into the reaction mass. After the completion of the reaction, the mixture was neutralized with phosphoric acid, and the formed potassium phosphate was filtered off under increased pressure to obtain a crude product. This product was purified by column chromatography on silica gel to remove the ethylene oxide adduct of polypropylene glycol to afford polyoxyethylene[2′-O-β-D-glucopyranosyl-β-D-glucopyranosyl)oxy]-alkane acid and -alkene acid methyl esters as a pale yellow paste.

Table 2

| Addition mole number | Amount of ethylene oxide used (g) | Crude product (g) |
|---|---|---|
| 5 | 34.4 | 132 |
| 7 | 48.2 | 145 |
| 15 | 103.3 | 200 |
| 30 | 206.6 | 305 |

IR (cm$^{-1}$): 3380~3200 (—OH); 1740 (>C=O ester); 1100 (—O—).

Table 3

| | Oil Characterization Analyses | | | |
|---|---|---|---|---|
| | Hydroxy value | Acid value | Saponification value | Ester value |
| 5 moles adduct | 463.5 | 0.5 | 67.0 | 66.5 |
| (Calculated) | (458.4) | (0) | (65.5) | (65.5) |
| 7 moles adduct | 420.1 | 1.2 | 60.9 | 59.7 |
| (Calculated) | (415.7) | (0) | (59.4) | 59.4) |
| 15 moles adduct | 311.3 | 0.7 | 45.2 | 44.5 |
| (Calculated) | (302.9) | (0) | (43.3) | (43.3) |
| 30 moles adduct | 205.8 | 0.7 | 30.0 | 29.3 |

Table 3-continued

| | Oil Characterization Analyses | | | |
|---|---|---|---|---|
| | Hydroxy value | Acid value | Saponification value | Ester value |
| (Calculated) | (200.7) | (0) | (28.7) | (28.7) |

From the results obtained by the above oil characterization analyses, it was ascertained that a specified amount of ethylene oxide was added.

INVENTIVE EXAMPLE 2

A 100 g amount of the mixture of [(2'-O-β-D-glucopyranosyl-β-D-glucopyranosyl)oxy]-alkane acid and -alkene acid methyl esters, and polypropyleneglycol obtained in Reference Example 1 was placed in an autoclave together with 0.25 g of potassium hydride, and the mixture was reacted at 100°–120° C. for 6 hours with an amount of a propylene oxide gas corresponding to the addition mole number shown in Table 4 being passed into the reaction mass. After the completion of the reaction, the mixture was neutralized with phosphoric acid and filtered under increased pressure to obtain a crude product as a brown paste. This product was purified by column chromatography on silica gel to afford polypropylene[(2'-O-β-D-glucopyranosyl-β-D-glucopyranosyl)oxy]-alkane acid and -alkene acid methyl esters as a pale yellow paste.

Table 4

| Addition mole number | Amount of propylene oxide used (g) | Crude product (g) |
|---|---|---|
| 5 | 45.4 | 143 |
| 7 | 63.55 | 158.5 |
| 15 | 136.2 | 230 |
| 30 | 272.4 | 365 |

IR (cm$^{-1}$): 3380~3200 (—OH); 1740 (>C=O ester); 1100 (—O—).

Table 5

| | Oil Characterization Analyses | | | |
|---|---|---|---|---|
| | Hydroxy value | Acid value | Saponification value | Ester value |
| 5 moles adduct | 430.1 | 0.8 | 62.6 | 61.8 |
| (Calculated) | (432.8) | (0) | (60.5) | (60.5) |
| 7 moles adduct | 382.3 | 0.7 | 53.7 | 53.0 |
| (Calculated) | (376.7) | (0) | (53.8) | (53.8) |
| 15 moles adduct | 271.0 | 1.0 | 39.5 | 38.5 |
| (Calculated) | (260.7) | (0) | (37.2) | (37.2) |
| 30 moles adduct | 170.7 | 0.7 | 25.3 | 24.6 |
| (Calculated) | (165.3) | (0) | (23.6) | (23.6) |

From the results obtained by the above oil characterization analyses, it was ascertained that a specified amount of propylene oxide was added.

INVENTIVE EXAMPLE 3

(i) A 100 g amount of a mixture of [(2'-O-β-D-glucopyranosyl-β-D-glucopyranosyl)oxy]-alkane acid and -alkene acid methyl esters, and polypropyleneglycol obtained in Reference Example 1 30 g of water and 70 g of ethanol were placed in a 500 ml round bottom flask. The mixture was stirred to obtain a homogeneous solution. To this solution was added 9 g of potassium hydroxide, and the resulting mixture was reacted under reflux conditions for 2 hours. After the completion of the reaction, the mixture was neutralized with sulfuric acid, and the potassium sulfate formed was filtered off. The filtrate was placed in a 500 ml three-necked flask equipped with a Liebig condenser and was evaporated under normal pressure to remove methanol and ethanol. Thereafter, water was distilled off under reduced pressure to yield [(2'-O-β-D-glucopyranosyl-β-D-glucopyranosyl)oxy]-alkane acid and -alkene acid.

(ii) The product thus obtained by process (i) above was placed in an autoclave together with 0.25 g of potassium hydroxide, and the mixture was reacted at 100°–120° C. for 6 hours with an amount of propylene oxide gas corresponding to the addition mole number shown in Table 6 being passed into the reaction mass. After the completion of the reaction, the mixture was neutralized with phosphoric acid and filtered under increased pressure to obtain a brownish viscous crude product. This product was purified by column chromatography on silica gel to afford polyoxypropylene [(2'-O-β-D-glucopyranosyl-β-D-glucopyranosyl)oxy]-alkane acid and -alkene acid methyl esters as pale yellow paste.

Table 6

| Addition mole number | Amount of propylene oxide (g) | Crude product (g) |
|---|---|---|
| 5 | 45.2 | 143 |
| 8 | 72.2 | 168 |
| 15 | 135.4 | 230 |
| 30 | 270.8 | 366 |

IR (cm$^{-1}$): 3380~3200 (—OH); 1740 (>C=O ester); 1100 (—O—).

Table 7

| | Oil Characterization Analyses | | | |
|---|---|---|---|---|
| | Hydroxy value | Acid value | Saponification value | Ester value |
| 5 moles adduct | 501.2 | 0.9 | 63.2 | 62.3 |
| (Calculated) | (491.9) | (0) | (61.5) | (61.5) |
| 8 moles adduct | 421.4 | 0.7 | 53.4 | 52.7 |
| (Calculated) | (412.8) | (0) | (51.6) | (51.6) |
| 15 moles adduct | 305.3 | 0.7 | 38.9 | 38.2 |
| (Calculated) | (299.1) | (0) | (37.4) | (37.4) |
| 30 moles adduct | 182.0 | 0.3 | 24.8 | 24.5 |
| (Calculated) | (188.0) | (0) | (23.5) | (23.5) |

From the results obtained by the above oil characterization analyses, it was ascertained that a specified amount of propylene oxide was added.

INVENTIVE EXAMPLE 4

Addition of ethylene oxide to glycolipid octyl ester:

A 20 g amount of a glycolipid methyl ester-polypropylene glycol mixture was placed in an autoclave, and to this mixture were added 4.2 g of actyl alcohol and 5 g of methanol to obtain a homogeneous solution, then 0.1 g of sodium methylate. The greater part of methanol was distilled off at 70° C., and an ester interchange reaction was carried out while methanol which formed was distilled off with stirring under a reduced pressure of 250 mmHg. The reaction progress was observed by gas chromatography under the following conditions: glass column; 3% silicon JXR-Chromsolve W having 60~80 meshes; inside diameter 3 mm; height 1 m; column oven temperature of 250° C.~350° C; pressure by helium gas of 0.6 kg/cm$^2$; and hydrogen flame detecter as a detector. The reaction state was measured from the peak area ratio of the glucolipid methyl ester and glycolipid octyl ester with a sample picked up from the reaction solution and trimethyl-sililated with a trimethyl-sililating agent. The reaction was regarded as having been completed when the peak of the glycolipid methyl ester disappeared. The mixture was reacted at 100°–120° C. for 6 hours with an ethylene oxide gas in an amount specified in Table 8 being passed into the reaction mass, to obtain an ethylene oxide adduct. The amount of ethylene oxide was varied according to the specified addition mole number as shown in Table 8.

Table 8

| Addition mole number | Amount of ethylene oxide (g) | Crude product (g) |
|---|---|---|
| 7 | 9.8 | 33.5 |
| 15 | 20.9 | 44.6 |
| 30 | 41.8 | 65.0 |

The mixture was neutralized with phosphoric acid, and the formed sodium phosphate was filtered off under increased pressure. A 5 g amount of the sample was purified by column chromatography on 500 g of silica gel (chloroform-methanol; gradient elution) to obtain polyoxyethylene [(2'-O-β-D-glucopyranosyl-β-D-glucopyranosyl)oxy]-alkane acid and -alkene acid octyl ester fractions which amounted to 91 to 94% by weight of the whole sample weight.

IR (cm$^{-1}$): 3380~3200 (—OH); 1740 (>C=O); 1100 (—O—: ether); 1050 (—OH).

Table 9

| | | Oil Characterization Analyses | | | |
|---|---|---|---|---|---|
| | | Hydroxy value | Acid value | saponification value | Ester value |
| 7 moles | Calculated | 376.5 | 0 | 53.8 | 53.8 |
| adduct | Found | 389.1 | 0.7 | 51.5 | 50.8 |
| 15 moles | Calculated | 281.5 | 0 | 40.2 | 40.2 |
| adduct | Found | 293.8 | 0.4 | 39.0 | 38.6 |
| 30 moles | Calculated | 191.1 | 0 | 27.3 | 27.3 |
| adduct | Found | 200.6 | 0.2 | 26.4 | 26.2 |

INVENTIVE EXAMPLE 5

Addition of ethylene oxide to glycolipid oleyl ester:
A 20 g amount of the mixture of glycolipid methyl ester-polypropylene glycol obtained in Reference Example 1 was placed in an autoclave, and to this mixture were added 8.9 g of oleyl alcohol, t g of methanol and then 0.1 g of sodium methylate. The reaction conditions for ester interchange and ethylene oxide addition were the same as in Inventive Example 4. 21.0 g of an ethylene oxide gas was reacted with the mixture and an adduct was obtained having an average addition number of 15. 29.8 g of the ethylene oxide adduct thus obtained was neutralized with phosphoric acid, and the formed sodium phosphate was filtered off under increased pressure. 5 g of the sample was purified by column chromatography under the same conditions as in Inventive Example 4 to afford 4.5 g of polyoxyethylene[2'-O-β-D-glucopyranosyl-β-D-glucopyranosyl)oxy]-alkane acid and -alkene acid oleyl ester fractions.

IR (cm$^{-1}$): 3380~3200 (—OH); 1740 (>C=O); 1100 (—O—: ether); 1050 (—OH).

Table 10

| | | Oil Characterization Analyses | | | |
|---|---|---|---|---|---|
| | | Hydroxy value | Acid value | Saponification value | Ester value |
| 15 moles | Calculated | 255.9 | 0 | 36.6 | 36.6 |
| adduct | Found | 261.1 | 0.8 | 35.0 | 34.2 |

INVENTIVE EXAMPLE 6

Addition of propylene oxide to glycolipid lauryl ester:
20 g of a mixture of glycolipid methyl ester-polypropylene glycol obtained in Reference Example 1 was placed in an autoclave, and to this mixture were added 6.1 g of lauryl alcohol, 5 g of methanol and then 0.1 g of sodium methylate. The method for preparing a glycolipid lauryl ester was the same as in Inventive Example 4. After the completion of the ester interchange reaction, the mixture was reacted at 100° to 120° C. for 6 hours, with a specified amount of a propylene oxide gas being passed into the reaction mass to obtain a propylene oxide adduct. The amount of the propylene oxide gas was varied according to the specified addition mole number as shown in Table 11.

Table 11

| Addition mole number | Amount of propylene oxide (g) | Crude product (g) |
|---|---|---|
| 7 | 12.87 | 38.3 |
| 15 | 27.56 | 52.1 |
| 30 | 55.12 | 80.2 |

The thus obtained propylene oxide adduct was neutralized with phosphoric acid, and the formed sodium phosphate was filtered off under increased pressure. 5 g of the sample was purified by column chromatography under the same conditions as in Inventive Example 4 to afford polyoxypropylene[(2'-O-β-D-glucopyranosyl-β-D-glucopyranosyl)oxy]-alkane acid and -alkene acid lauryl ester fractions which amounted to 90 to 93% by weight of the whole sample weight.

IR (cm$^{-1}$): 3380~3200 (—OH); 1740 (>C=O); 1100 (—O—: ether).

Table 12

| | | Oil Characterization Analyses | | | |
|---|---|---|---|---|---|
| | | Hydroxy value | Acid value | Saponification value | Ester value |
| 7 moles | Calculated | 328.1 | 0 | 46.9 | 46.9 |
| adduct | Found | 339.4 | 0.9 | 45.7 | 44.8 |
| 15 moles | Calculated | 236.5 | 0 | 33.8 | 33.8 |
| adduct | Found | 247.1 | 0.5 | 32.9 | 32.4 |
| 30 moles | Calculated | 155.2 | 0 | 22.2 | 22.2 |
| adduct | Found | 160.8 | 0.3 | 21.6 | 21.3 |

What is claimed is:
1. A hydroxyalkyl-etherified glycolipid ester represented by the formula (I),

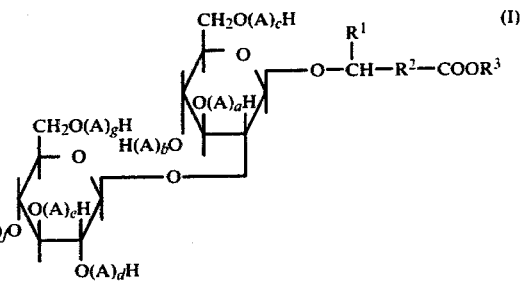

wherein $R^1$ represents methyl or hydrogen, $R^2$ represents a saturated or unsaturated hydrocarbon group having 11 to 15 carbon atoms when $R^1$ is methyl or, $R^2$ represents a saturated or unsaturated hydrocarbon group having 12 to 16 carbon atoms when $R^1$ is hydrogen, $R^3$ represents a saturated or unsaturated hydrocarbon group having 1 to 20 carbon atoms, A represents —$CH_2$—$CH_2$—O— or

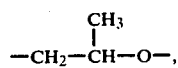

and a,b,c,d,e,f and g represent integers whose sum ranges from 1 to 60.

2. The hydroxyalkyl-etherified glycolipid ester according to claim 1, wherein a,b,c,d,e,f and g are integers whose sum ranges from 5 to 30.

3. A hydroxyalkyl-etherfified glycolipid ester represented by the formula (II),

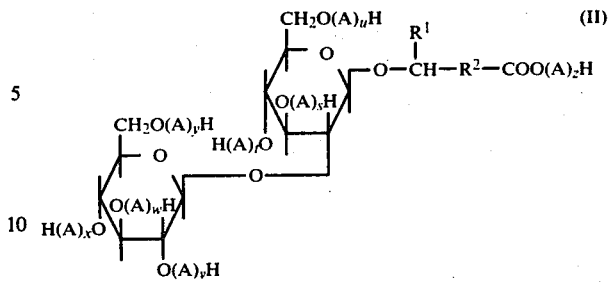

wherein $R^1$ represents methyl or hydrogen, $R^2$ represents a saturated or unsaturated hydrocarbon group having 11 to 15 carbon atoms when $R^1$ is methyl or, $R^2$ represents a saturated or unsaturated hydrocarbon group having 12 to 16 carbon atoms when $R^1$ is a hydrogen atom, A represents —$CH_2$—$CH_2$—O— or

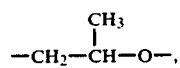

and s,t,u,v,w,x,y and z represent integers whose sum ranges from 1 to 60.

4. The hydroxyalkyl-etherified glycolipid ester according to claim 3, wherein s,t,u,v,w,x,y and z are integers from 5 to 30 in the sum total in the formula (II).